(12) United States Patent
Esposito et al.

(10) Patent No.: US 7,027,358 B1
(45) Date of Patent: Apr. 11, 2006

(54) SYSTEM FOR PRESSURE ULCER PROPHYLAXIS AND TREATMENT

(75) Inventors: Roy A. Esposito, Boynton Beach, FL (US); Steven Antokal, Coral Springs, FL (US)

(73) Assignee: Advanced Prevention Technologies Inc., Coral Springs, FL (US)

( * ) Notice: Subject to any disclaimer, the term of this patent is extended or adjusted under 35 U.S.C. 154(b) by 367 days.

(21) Appl. No.: 10/423,809

(22) Filed: Apr. 28, 2003

(51) Int. Cl.
G04B 47/00 (2006.01)
G04F 8/00 (2006.01)
G04F 10/00 (2006.01)
G08B 23/00 (2006.01)

(52) U.S. Cl. .................. 368/10; 368/109; 368/112; 368/250; 5/715; 600/587; 600/592; 340/573.1; 340/573.5

(58) Field of Classification Search .............. 368/10, 368/89, 97, 98, 107–109, 112, 243, 250; 340/573.1, 573.7, 666, 573.5; 600/592, 595, 600/587; 5/710, 713, 715

See application file for complete search history.

(56) References Cited

U.S. PATENT DOCUMENTS

| | | | |
|---|---|---|---|
| 4,225,852 A | 9/1980 | Waters et al. | |
| 4,554,930 A | 11/1985 | Kress | |
| 5,542,136 A * | 8/1996 | Tappel | 5/710 |
| 5,561,412 A * | 10/1996 | Novak et al. | 340/286.07 |
| 5,583,832 A | 12/1996 | DePonty | |
| 5,699,038 A * | 12/1997 | Ulrich et al. | 340/286.07 |
| 5,751,214 A * | 5/1998 | Cowley et al. | 340/573.4 |
| 5,963,137 A | 10/1999 | Waters, Sr. | |
| 6,014,346 A | 1/2000 | Malone | |
| 6,030,351 A * | 2/2000 | Schmidt et al. | 600/592 |
| 6,129,686 A * | 10/2000 | Friedman | 600/595 |
| 6,287,253 B1 | 9/2001 | Ortega et al. | |
| 6,320,510 B1 * | 11/2001 | Menkedick et al. | 340/573.1 |
| 6,384,728 B1 * | 5/2002 | Kanor et al. | 340/573.1 |
| 6,646,556 B1 * | 11/2003 | Smith et al. | 340/573.1 |
| 6,847,301 B1 * | 1/2005 | Olson | 340/666 |
| 6,897,781 B1 * | 5/2005 | Cooper et al. | 340/573.1 |
| 2004/0046668 A1 * | 3/2004 | Smith et al. | 340/573.7 |

* cited by examiner

Primary Examiner—Kamand Cuneo
Assistant Examiner—Jeanne-Marguerite Goodwin
(74) Attorney, Agent, or Firm—Seth Natter; Natter & Natter (57) ABSTRACT

A system for pressure ulcer prophylaxis and treatment includes an annunciator which is attached to the outer face of the door or to the doorway of a patient's room and a bedside patient position sequence indicator. The annunciator includes a timing device with settable cycle duration and provides both visual and audible signals to indicate that a prescribed patient turning regimen cycle now requires repositioning of the patient. The annunciator generates a first signal when the cycle duration enters an expiry window and generates a different, intensified signal after the cycle has ended without being reset by a caregiver. The patient position sequence indicator includes a visual display which advises a caregiver of the position in which the patient was last placed and the next sequential position to which the patient is to be moved.

19 Claims, 7 Drawing Sheets

SYSTEM FOR PRESSURE ULCER PROPHYLAXIS AND TREATMENT

BACKGROUND OF THE INVENTION

1. Field of the Invention

This invention relates generally to the prevention and treatment of pressure ulcers and more particularly to a system for assuring the faithful execution of a patient-repositioning regimen.

2. Antecedents of the Invention

The prevention and treatment of pressure ulcers is a significant aspect of medical care and treatment of patients at virtually all types of healthcare facilities. Indeed, pressure or pressure ulcers are a major risk for critically ill patients in hospital intensive care units, as well as the general hospital patient population, patients in long-term care facilities and patients in a home care environment.

Pressure ulcers comprise lesions resulting from reduced blood flow and/or irritation in areas over bony prominences. Unrelieved pressure at contact surfaces with a bed mattress, splint, cast or other hard object over a prolonged period constitutes the major contributing factor to reduced blood flow.

Pressure ulcers generally form at the sacrum, ischium, iliac crest, greater trochanter and at the calcaneus and external malleous. Prolonged exposure to pressure at such sites reduces the flow of blood which impedes delivery of oxygen, resulting in tissue hypoxia. Movement of the patient shifts the pressure such that the blood supply to the skin is not impaired for prolonged periods. Patients who cannot move, however, are at greater risk for developing pressure ulcers.

Among the pressure ulcer risk factors are decreased mobility, increased age, decreased cognitive abilities, nerve damage which results in diminished ability to sense pain, medications, incontinence, poor nutrition, as well as physical contact parameters, e.g. friction, shear forces, pressure levels and duration of applied pressure.

Malnourished patients may lack a protective layer of fat under the skin around bony projections and are at increased risk. In certain instances when circulation is only partially impeded, friction and shear forces due to wrinkled bedding, for example, may constitute contributing factors as well as exposure to urine or feces.

A crucial aspect of any program for prevention or treatment of pressure ulcers has been the maintenance of a patient-repositioning regimen. The use of pressure reducing mattresses without maintenance of a patient-repositioning regimen has proven insufficient.

While many long-term healthcare facilities provided caregivers with patient repositioning schedules on charts or the like, the maintenance of such schedules was not an easy task for caregivers. Different patients were on different schedules, e.g. turning cycle start time and/or cycle duration. Determinations were often required to be made by the caregiver as to the next sequential patient position. Often, a prescribed repositioning sequence was not followed due to misreading positioning information on the schedule, caregiver distractions during patient repositioning, etc.

In U.S. Pat. No. 6,014,346 to MALONE, there is disclosed a device for timing and monitoring patient sedentary inactivity which is operatively connected to a patient position sensor, a nurse call station, a remotely positioned light, etc. The MALONE device lacked portability and ease of setup. Further, the sequence of positions was not preprogrammed, such that deviations from a prescribed position sequence could occur when the healthcare provider repositioned the patient.

SUMMARY OF THE INVENTION

A system for pressure ulcer prophylaxis and treatment comprises a self-contained caregiver alert annunciator which includes a timing device having a settable cycle duration. The annunciator is positioned at the door of a patient's room facing a hallway. The system also includes a self-contained patient position sequence indicator situated at the foot of a patient's bed or elsewhere adjacent the patient.

The annunciator carries visual and/or audible attention directing signaling devices which indicate the approaching end of a prescribed cycle, and which generate a different, intensified signal after a cycle has ended without being reset by the caregiver. Safeguards against tampering by the patient's visitors as well as against resetting the cycle prior to entering a cycle expiry window are provided. The annunciator also includes a low power consumption battery life prolongation standby mode and automatically switches to a full power mode for energizing the signal generator when the lapsed cycle time enters the cycle expiry window.

The patient position sequence indicator includes a visual display which advises the caregiver of the current and/or next sequential position to which the patient is to be moved. A low power consumption battery life prolongation standby mode and anti-tamper safeguards are also provided.

From the foregoing compendium, it will be appreciated that it is an aspect of the present invention to provide a system for pressure ulcer prophylaxis and treatment, which is not subject to the disadvantages of the antecedents of the invention aforementioned.

A feature of the present invention is to provide a system for pressure ulcer prophylaxis and treatment of the general character described which is simple to use by relatively unskilled caregivers.

A consideration of the present invention is to provide a system for pressure ulcer prophylaxis and treatment of the general character described which assures scrupulous maintenance of a prescribed patient repositioning regimen.

Another aspect of the present invention is to provide a system for pressure ulcer prophylaxis and treatment of the general character described which is economical in operation.

An additional consideration of the present invention is to provide a system for pressure ulcer prophylaxis and treatment of the general character described, which provides extended battery life.

A further aspect of the present invention is to provide a system for pressure ulcer prophylaxis and treatment of the general character described which is portable and may be easily set up without the necessity of hard-wired connections within a patient care facility or between the components of the system.

Yet a further feature of the present invention is to provide a system for pressure ulcer prophylaxis and treatment of the general character described which is tamper resistant, thus assuring that a patient will be meticulously maintained on a prescribed repositioning cycle regimen.

A further consideration of the present invention is to provide a system for pressure ulcer prophylaxis and treatment of the general character described which is well adapted for economical mass production fabrication.

Other aspects, features and considerations in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings in which are shown some of the various possible exemplary embodiments of the invention.

DESCRIPTION OF THE PREFERRED EMBODIMENTS

Figure 1:
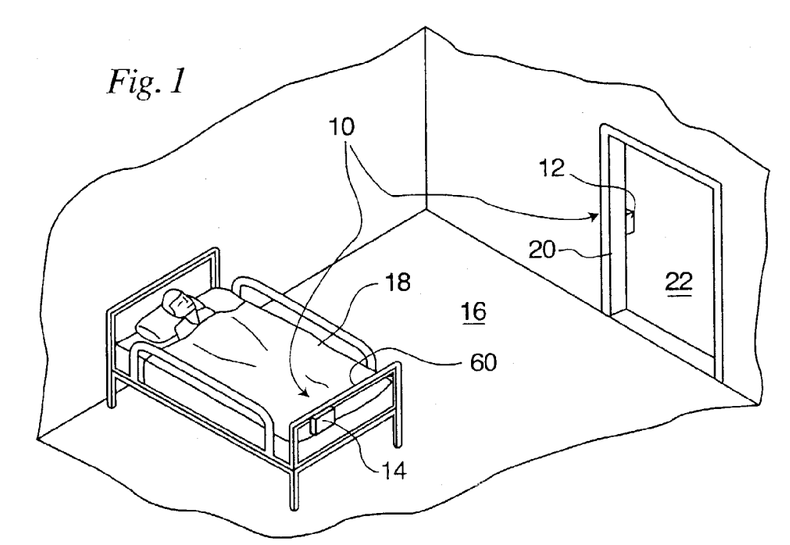
FIG. 1 is a fragmentary perspective illustration of a bedridden patient's room at a healthcare facility and illustrating a system for pressure ulcer prophylaxis and treatment constructed in accordance with and embodying the invention including an annunciator secured to an outer doorway and a position sequence indicator at the patient's bedside.

Referring now in detail to the drawings wherein some of the various possible exemplary embodiments of the invention are shown, the reference numeral 10 denotes generally a system for pressure ulcer prophylaxis and treatment constructed in accordance with and embodying the invention. The system 10 comprises two self-contained units, an annunciator 12 and a patient position sequence indicator 14. The system 10 is employed in the environment of a patient's room 16 at a care facility such as a hospital, long-term care facility, nursing facility, home care environment, etc. A bedridden patient having decreased mobility is depicted in a bed 18.

In accordance with the invention, the annunciator 12 is stationed at an entranceway to the room 16, such as being adhered to the outer face of a doorway 20 or to door of the room and is thus positioned within or facing a hallway 22 of the facility so as to be easily noticed by caregivers making rounds, etc.

Figure 2:
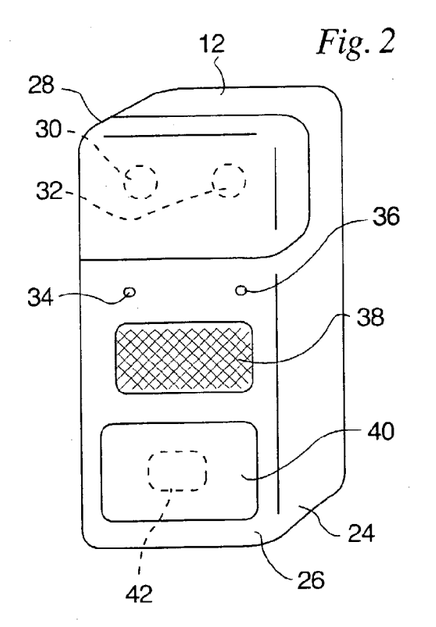
FIG. 2 is a front perspective view of the annunciator showing a plurality of high intensity light emitting diodes covered by a translucent lens, a passageway through the front of the cabinet for the emission of an audible alert signal and a flexible panel covering a reset switch.

With reference to FIG. 2, the annunciator 12 includes a housing 24 having a front panel 26. Mounted to the front panel 26 is a translucent cover 28 which overlies a pair of caregiver attention directing high intensity light emitting diodes (LED's) or LED arrays, 30, 32 which emit light of different colors. The LED 30 emits yellow or amber, for example, and the LED 32 emits red, for example.

Exposed through the front panel 26 are a pair of status indicator LED's 34, 36 with the LED 34 emitting green and the LED 36 emitting white, for example. An array of perforations 38 in the front panel is for the transmission of an audible alert signal and a flexible film 40 may overly a single caregiver accessible timing cycle reset switch 42.

Figure 3:
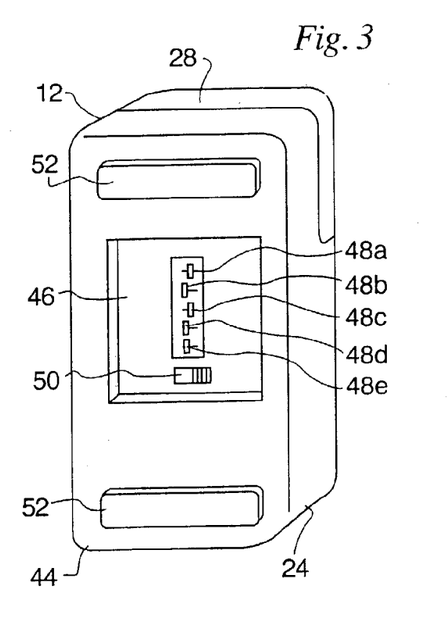
FIG. 3 is a rear perspective view of the annunciator with an access panel removed illustrating a concealed compartment within which is mounted cycle programming switches.

In FIG. 3, there is illustrated a rear panel 44 of the annunciator 12. The rear panel 44 includes a concealed recessed compartment 46, the cover of which has been removed. Upon removal of the cover, a plurality of programming DIP switches 48a, 48b, 48c, 48d and 48e are rendered accessible. The purpose and function of the programming switches will be explained hereinafter. Also rendered accessible by removal of the cover is a power switch 50. A battery compartment (not illustrated) carries a suitable battery power supply.

In order to mount the annunciator 12 at a suitable location facing or within the hallway 22, a pair of mounting strips 52 are adhered to the rear panel 44. The mounting strips 52 may comprise adhesive backed magnetic tape or, in the event the outer face of the door to the patient's room and/or the door frame 20 are not fabricated of ferrous material, the strips 52 may comprise lengths of hook and loop type fastener which are joined to corresponding lengths adhered to the door, door frame or hallway wall adjacent the doorway.

Figure 4:
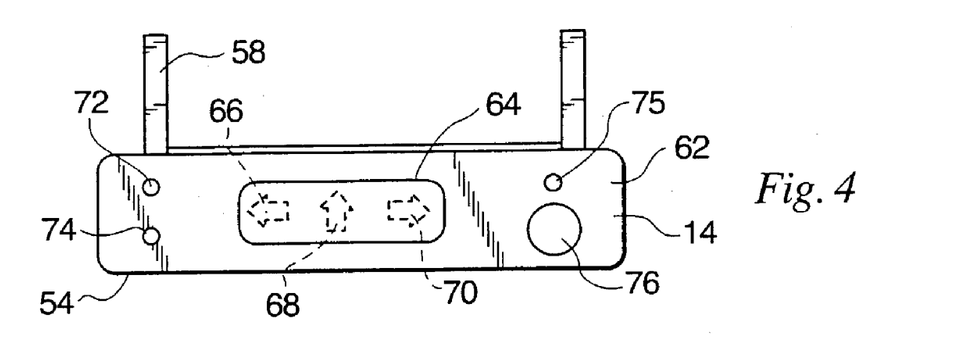
FIG. 4 is a top plan view of the position sequence indicator showing a display for indicating one of a plurality of patient positions.
Figure 5:
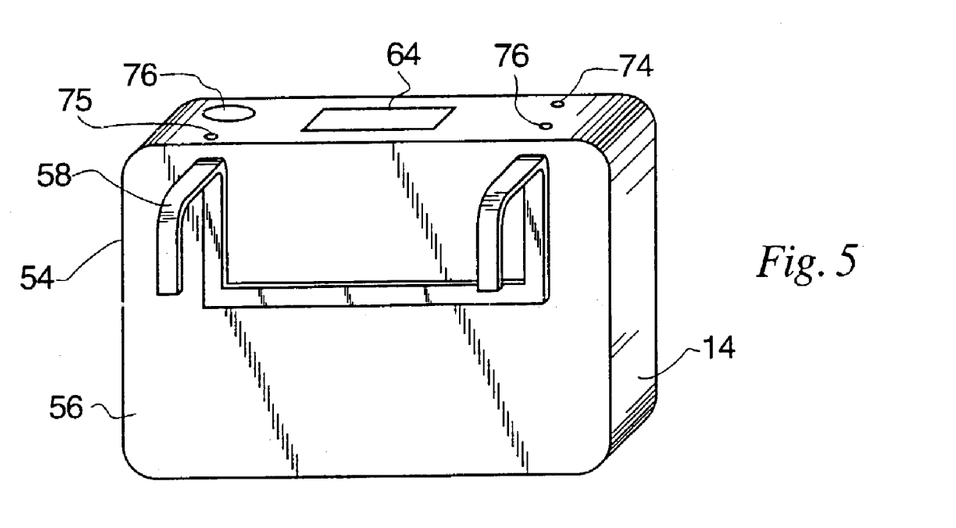
FIG. 5 is a rear perspective view of the position sequence indicator.
Figure 6:
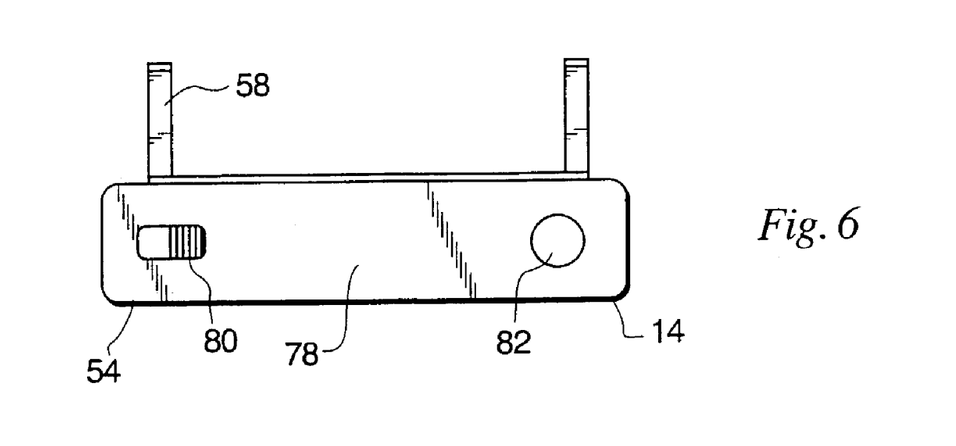
FIG. 6 is a bottom view of the position sequence indicator showing controls normally concealed from view.

Referring now to FIGS. 4 through 6 wherein the position sequence indicator 14 is illustrated, it should be noted that the position sequence indicator 14 includes a housing 54 having a rear panel 56. A removable bracket 58 or other attachment for mounting the position sequence indicator 14 in the room 16 on or adjacent the bed 18 is fixed to the rear panel 56. The bracket 58 may be employed to suspend the position sequence indicator 14 from a rail 60 at a foot of the patient's bed 18, as illustrated in FIG. 1.

It should be noted that the position sequence indicator 14 may be attached to, carried on or mounted to a shelf, a side rail of the bed 18, a night stand or even a wall adjacent the patient's bed. Pursuant to the invention, however, the patient position sequence indicator 14 is to be positioned in close proximity to the patient.

At a top panel 62 of the housing 54 there is a patient position display 64 which includes discrete visual patient position indicators, e.g. left, supine, and right, which are illuminated from behind by LED's 66, 68, 70 respectively, or other suitable light sources such as an LCD. The display 64 may comprise interchangeable opaque panels with masked translucent position indicators for alternate position symbols and/or language formats. There is additionally provided, on the top panel 62, differently colored status indicator LED's 72, 74 and 75 and a single caregiver actuation push button switch 76.

The position sequence indicator housing 54 also includes a bottom panel 78 which is not normally viewable. A power switch 80 and an initializing switch 82 are found on the bottom panel. The housing 54 also includes a battery compartment (not illustrated).

The system 10 for pressure ulcer prophylaxis and treatment is relatively simple to set up and easy to use. To program a prescribed patient repositioning regimen cycle at the annunciator 12, the cover is removed from the recessed compartment 46 and the DIP switches are set to positions indicating the prescribed cycle time, e.g. one half hour (48a), one hour (48b), two hours (48c), etc., whether or not an audible alarm is to be actuated (48d) or to set a demonstration or test mode rapid cycle (48e). Additionally, the power switch 50 is actuated. Thereafter, the recessed compartment 46 is covered and the annunciator 12 is mounted to the door frame 20, the outer face of the door or the wall of the hallway 22.

The green LED 34 will illuminate, indicating that a prescribed timing cycle has commenced. After a brief period, e.g. 15 seconds, the annunciator 12 enters a low power consumption standby mode and the white status LED 36 is illuminated while the green LED 34 is extinguished. The circuit of the annunciator 12 maintains the white LED 36 illuminated for the duration of the low power consumption standby mode.

After the annunciator 12 has been set up, the caregiver immediately proceeds into the patient's room 16 and actuates the position sequence indicator 14. Set up of the position sequence indicator 14 includes turning on the power switch 80, whereupon one of the position indicators, e.g. the supine indicator 68, is illuminated. If an alternate "initial" (precycle commencement) position is desired, the initializing switch 82 is depressed and held until the desired precycle commencement position is illuminated. Simultaneous with illumination of the "initial" position indicator, the red status LED 72 flashed to indicate that this is the position of the patient prior to repositioning which is now about to occur.

The caregiver then mounts the position sequence indicator 14 at the foot of the patient's bed or otherwise in the proximity of the patient and depresses the push button 76 for a prescribed duration, e.g. 10 seconds. After the 10 second period, the next sequential position indicator, e.g. the right position indicator 70, will illuminate, the flashing red status LED 72 will be extinguished, and the green status LED 74 will be illuminated.

As an anti-tampering feature, the position sequence indicator 14 will not advance the position indicator LED's 66, 68, 70 in response to actuation of the push button switch 76 for the duration of a lock out period, e.g. 20 minutes, which is shorter than the minimum cycle duration programmable on the annunciator.

After a predetermined duration, e.g. one minute, the power supply to the position indicators—66, 68, 70 and the green status indicator LED 74 are extinguished, however, the white status indicator LED 75 will be illuminated as the position sequence indicator circuit enters a low power consumption standby mode.

At any time, a caregiver may check to verify that the patient is in the prescribed position by depressing the push button switch 76, which will simultaneously illuminate the position indicator LED 66, 68 or 70 which has been prescribed for the current cycle together with the red status LED 72. The caregiver may then tend to rounds caring for other patients or attend to other duties.

When the prescribed cycle enters the cycle expiry window, e.g. fifteen minutes prior to the end of the cycle, the yellow caregiver attention directing LED or LED arrays 30 will commence flashing in the hallway 22 to alert the patient's caregiver that it is appropriate to reposition the patient. In the event the caregiver does not reset the annunciator 12 and reposition the patient during the cycle expiry window, the annunciator then enters a post expiry window, e.g. fifteen minutes, wherein the annunciator circuit actuates the attention directing red LED or LED array 32 at an initial flash rate and the LED 30 is extinguished. Upon conclusion of the post expiry window without resetting the annunciator 12, the annunciator circuit actuates the red LED or LED array 32 at an increased flash rate and may optionally energize an attention directing piezoelectric sound generator 84 (if the DIP switch 48d has been set) while maintaining the red LED 32 flashing at the faster rate, notifying the caregiver that repositioning of the patient is overdue.

The caregiver resets the annunciator cycle by merely depressing the switch 42 and holding the switch in such position for a prescribed duration, e.g. 10 seconds. By maintaining the switch depressed for the prescribed duration, the annunciator circuit enters a new timing cycle.

Immediately after resetting the annunciator, the caregiver proceeds to the patient and depresses the position sequence indicator push button 76. The position sequence indicator circuit thereafter illuminates the patient's current position concurrently with the status LED 72. If the push button switch 76 is depressed for the prescribed duration, e.g. 10, seconds, the position sequence indicator circuit then energizes the next sequential position indicator LED along with the status LED 74. The caregiver then repositions the patient to the new position shown in the display 64 and may leave the patient unless the caregiver is to administer other attendant care.

Both the annunciator 12 and the position sequence indicator 14 are reset to the next sequential cycle by merely depressing and holding a single switch at each unit for a prescribed duration, thus simplifying system operation.

Figure 7:
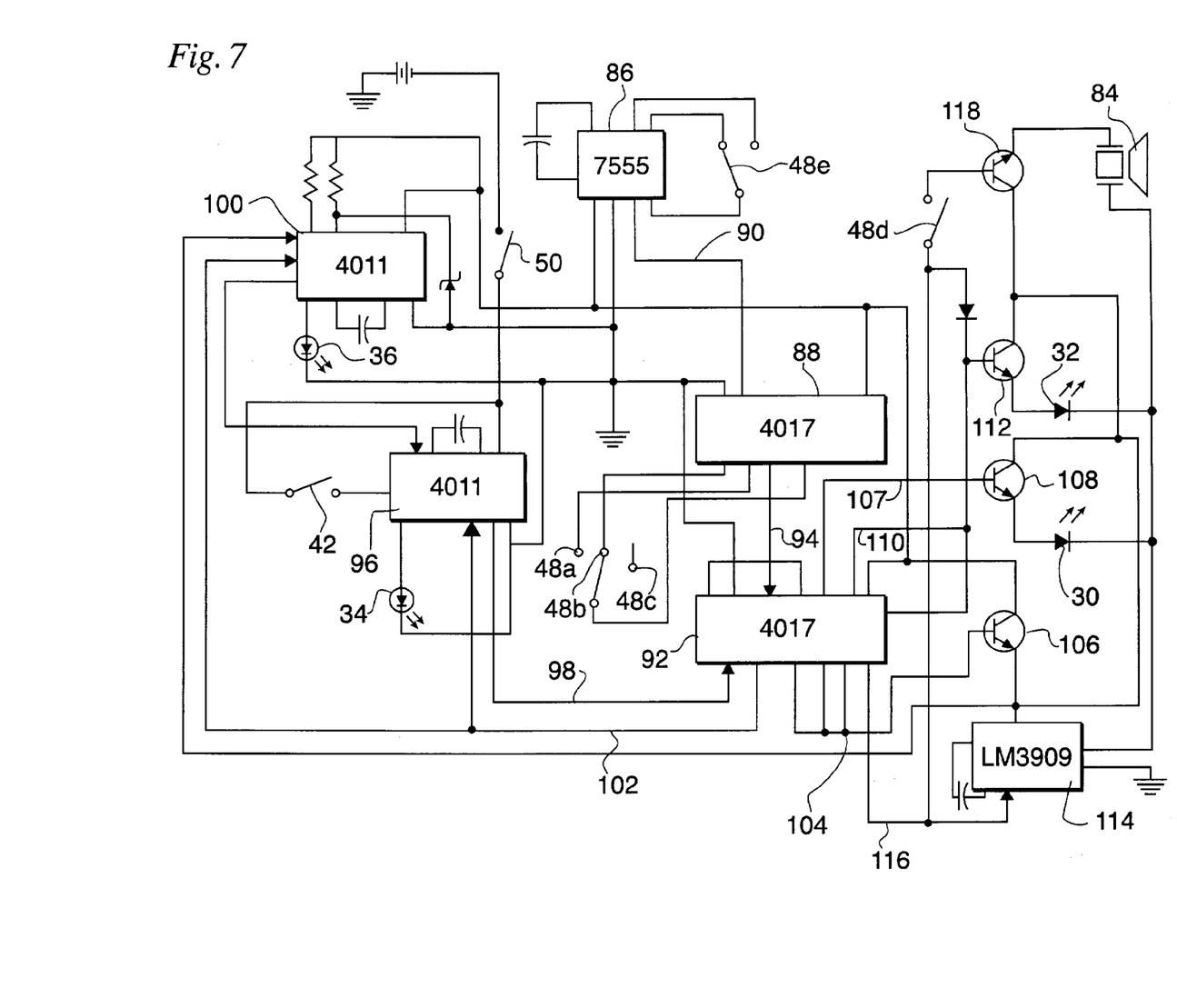
FIG. 7 is a schematized block diagram illustrating a typical circuit for the annunciator.

Referring now in detail to FIG. 7 wherein a simplified block diagram of a typical cycle timer circuit for the annunciator 12 is illustrated, it will be appreciated that the cycle timer circuit may be economically configured with relatively inexpensive integrated circuits having low power consumption to conserve battery life. Upon actuation of the power switch 50, a low power CMOS timer 86 generates pulses which are received at a decade counter 88 through a line 90. The decade counter 88 functions as a divider whose output is received at a further decade counter 92 through a line 94.

A NAND gate 96 is employed for switching with the output of the gate 96 being received at the counter 92 though a line 98. A cycle reset signal power from the push button switch 42 is received at the gate 96, with the ten-second delay achieved through a R/C timing circuit associated with the gate 96.

A further NAND gate 100 is employed for timing logic and for battery status monitoring and provides a low battery warning signal by flashing the white LED 36, which is otherwise steadily illuminated during the low power consumption standby mode of the patient repositioning cycle. An output signal from the gate 96 to the counter 92 along a line 98 constitutes the reset signal for commencement of a new repositioning cycle, while an output of the counter 92 to both of the gates 96, 100, along a line 102 constitutes a signal that the cycle duration has entered the expiry window and actuation of the push button 42 to reset a new cycle will be accepted.

A further output of the counter 92, along a line 104, is applied to a transistor 106 to switch the circuit to full power mode for energizing the yellow LED 30, the red LED 32 and the piezoelectric sound generator 84. An output signal from the counter 92 along a line 107 effects switching of a transistor 108 to actuate the yellow LED while an output signal along a line 110 effects switching of a transistor 112 for actuation of the red LED 32.

An integrated circuit flasher 114 is employed to flash the LED's 30, 32 with the flash frequency increased in the event the caregiver does not reset the cycle during the expiry window. The flasher 114 receives an increase flash rate control signal from the counter 92 along a line 116 is also employed to switch a transistor 118 for actuation of the piezoelectric sound generator 84, if so programmed.

The utilization of low power CMOS integrated circuits, utilization of the flasher 114, which limits power consumption of the LED's 30, 32 and the sound generator 84 as well as implementation of the low power consumption standby mode result in prolonged battery life.

Figure 8:
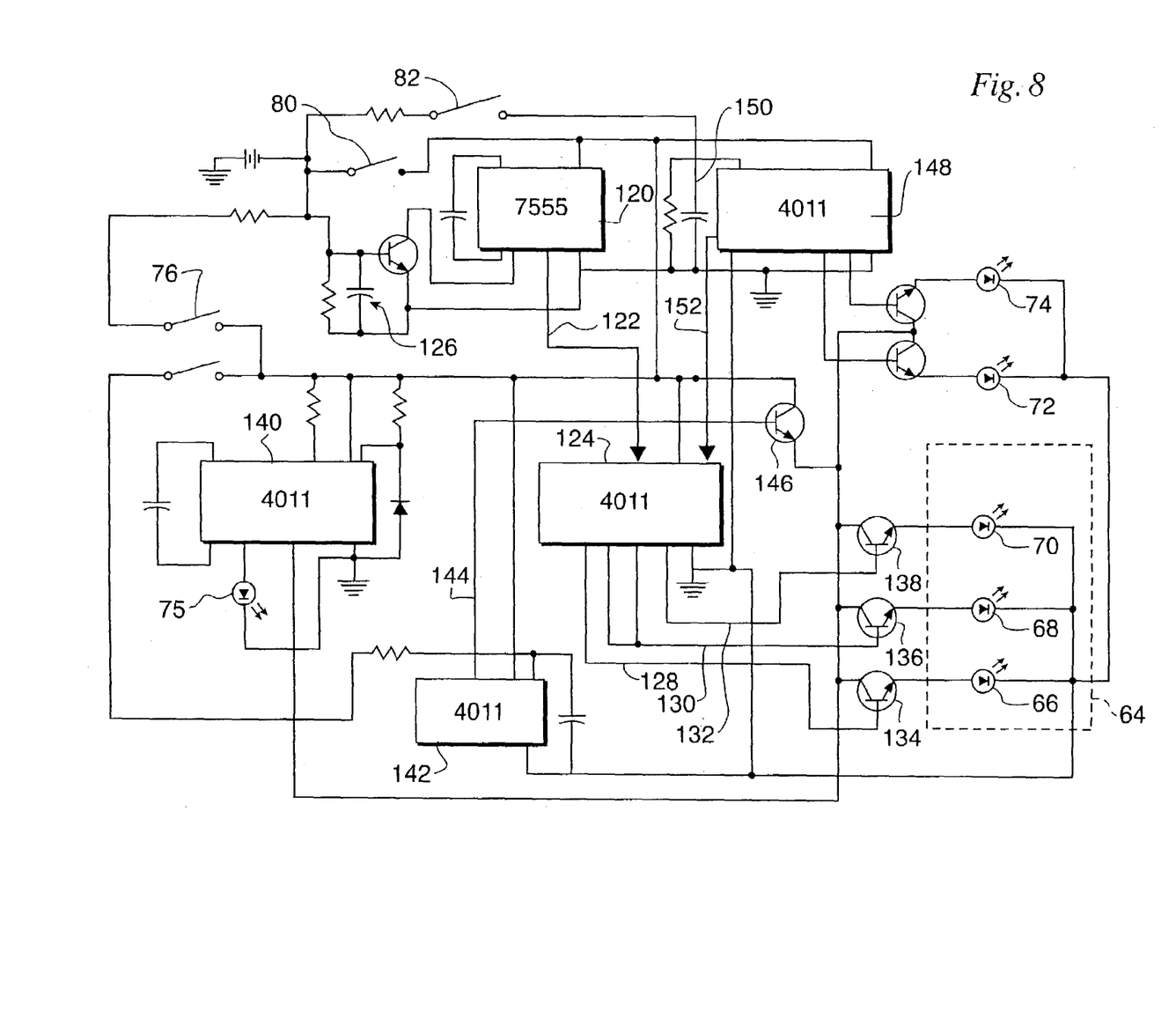
FIG. 8 is a schematized block diagram illustrating a typical position sequence indicator circuit.

Referring now to FIG. 8 wherein a schematized block diagram of a typical circuit for implementing the position sequence indicator 14 is disclosed, it should be noted that CMOS integrated circuits are employed.

The position sequence indicator 14 circuit includes a timer 120 which functions as a one shot, producing an output signal along a line 122 which signal is received at a decade counter 124.

The caregiver actuation push button switch 76 comprises a double pole single throw switch, the upper blade or leg of which functions to trigger the timer 120 with the 10 second hold down delay being effected through an R/C circuit 126. Upon receipt of each output pulse signal from the timer 120, the counter 124 sequentially generates a high output signal along one of the lines 128, 130, 132 respectively, which signal is applied to the base of one of the LED driving transistors 134, 136, 138 respectively. Each of the driving transistors 134, 136, 138 functions to illuminate its associated position indicator LED 66, 68, 70 respectively.

An integrated circuit gate 140 functions to drive the standby indicator LED 75 for the duration of the low power consumption mode and is employed for battery status monitoring to provide a low battery warning signal by flashing the LED 75.

A further integrated circuit gate 142 generates an output signal along a line 144 which is received at the base of a transistor 146 to switch the circuit to a full power mode to supply power to the position indicating LED's 66, 68, 70 when their respective transistors 134, 136, 138 are switched.

A further gate 148 is employed to control the status LED's 72, 74 through a pair of transistors. The gate 148 is also employed to effect a lock out which precludes sequencing the position indicator LED's within twenty minutes of the last sequencing. Timing is achieved through an R/C circuit 150. The gate 148 switches its output along a line 152 extending to an inhibit pin of the counter 124. With the counter 124 inhibited, during the lock out, reset signals generated by the timer 120 are not recognized.

Figure 9:
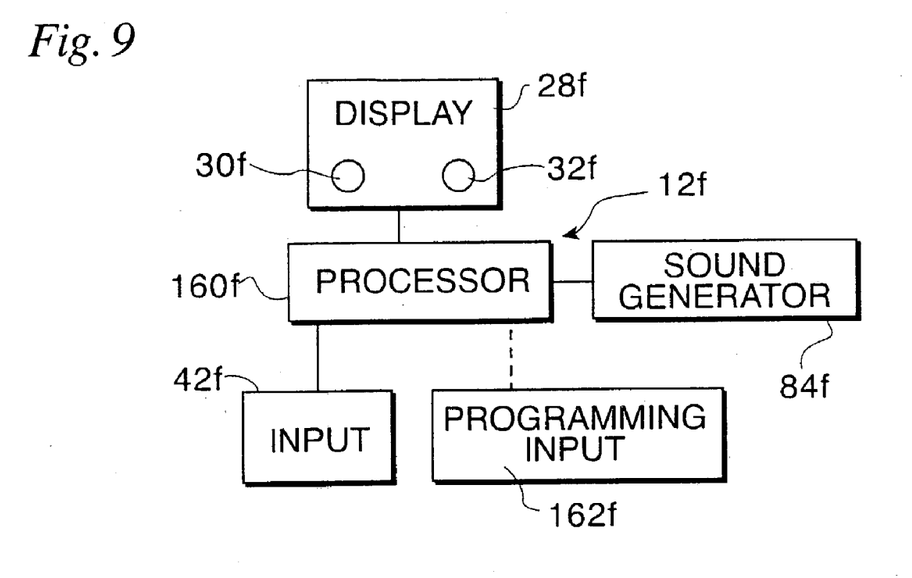
FIG. 9 is a block diagram of an alternate embodiment of the invention wherein an annunciator is processor implemented.

In FIG. 9 there is illustrated a processor implemented embodiment of the annunciator, with like reference numerals being employed to denote corresponding elements of the prior embodiment however, bearing the suffix "f".

A processor 160f functions as a cycle timer and is operatively coupled to a display 162f which carries two differently colored illumination devices, e.g. LED's 30f and 32f (which serve to direct the attention of the caregiver to the requirement for repositioning the patient). A caregiver input device comprising a push button reset switch 42f and a programming input device 162f which may comprise a keypad, either selectively attachable to the processor 160f or concealed in a recessed compartment of an annunciator housing, are also coupled to the processor 16f. The processor 160f is password protected, such that only authorized personnel will have the ability to utilize the keypad for programming.

Figure 10:
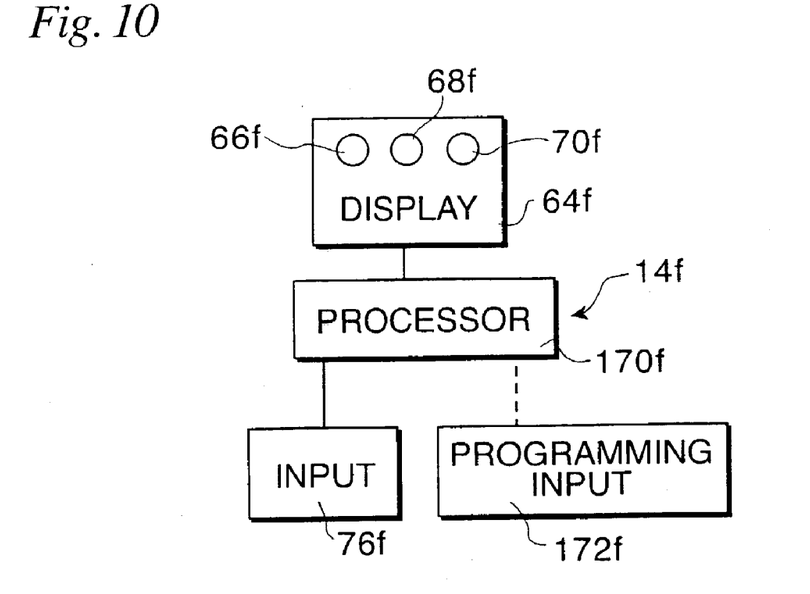
FIG. 10 is a schematized block diagram of an alternate embodiment of the invention wherein the patient position sequence indicator is processor implemented.

In FIG. 10 there is illustrated a processor implemented alternate embodiment of the position sequence indicator, with like numerals being employed to denote like components of the prior embodiment, however bearing the suffix "f". The position sequence indicator 14f of the alternate embodiment includes a processor 170f operatively coupled to a display 64f which carries discrete patient position status illumination devices 66f, 68f and 70f. The display 64f may optionally comprise any other visual position indicator, such as an LCD display panel.

A caregiver input push button switch 76f is also operatively coupled to the processor 170f as is an optional programming device 172f.

Figures 11, 12:
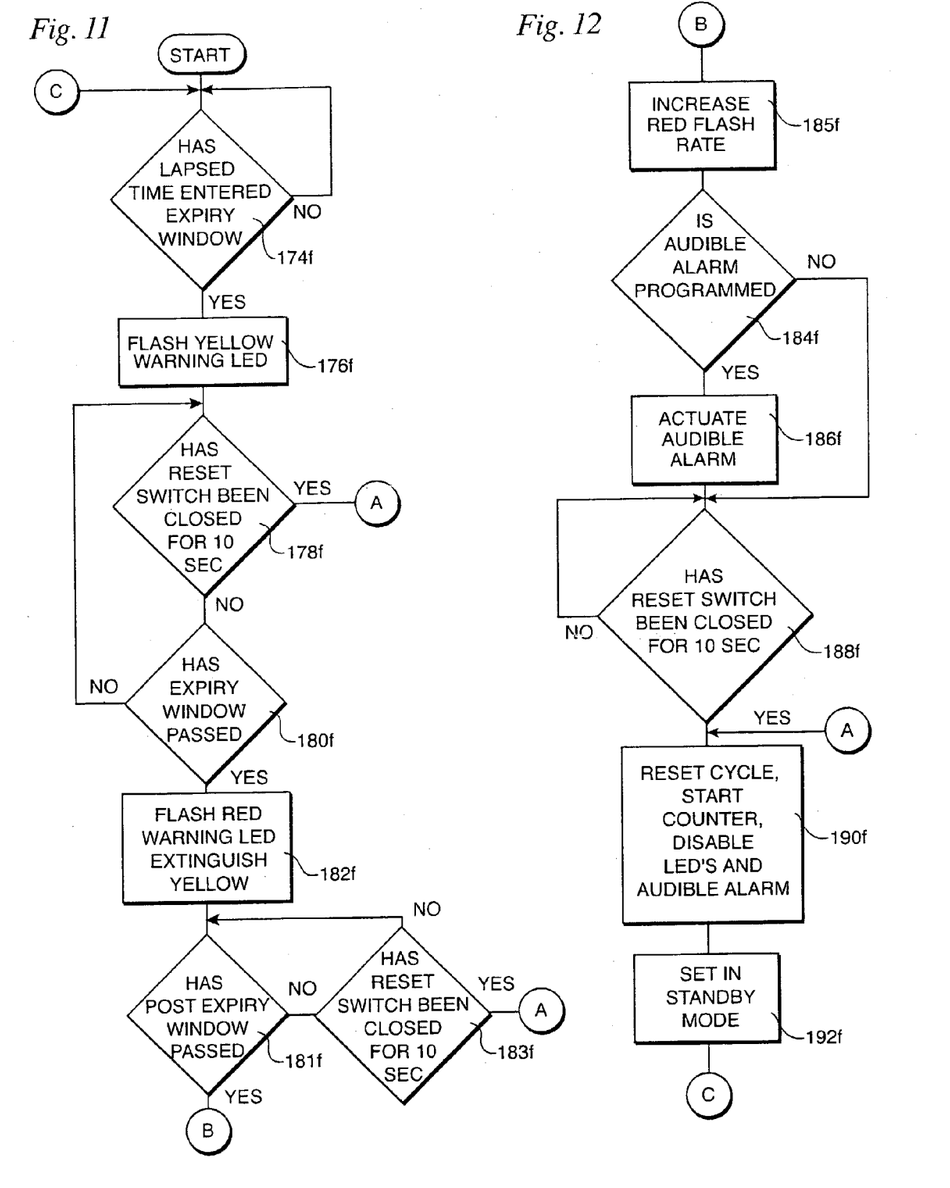
FIG. 11 is a schematized diagram of a typical routine for the processor implemented annunciator.
FIG. 12 is a continuation of the schematized diagram of the routine for the processor implemented annunciator.

In FIGS. 11 and 12 there is depicted a simplified schematized routine for the annunciator processor 160f in implementing and resetting a patient repositioning timing cycle in accordance with the invention. Upon entering the routine, an inquiry is made as to whether or not the cycle lapsed time has entered the expiry window, as indicated in a box 174f. In the event the expiry window has not been entered, the processor returns to the inquiry box 174f. In the event the cycle time has entered the expiry window, the processor 160f proceeds with flashing the warning yellow LED 30f, as indicated in a block 176f.

Thereafter, an inquiry is presented as to whether or not the reset switch 42f has been closed for the requisite duration, e.g. 10 seconds, as indicated in at an inquiry block 178f. In the event the reset switch 42f has been closed for the requisite duration, the processor proceeds with resetting as will be described in greater detail hereinafter.

In the event the reset switch has not been closed for the requisite duration, a further inquiry is made as to whether or not the expiry window has passed, as indicated in an inquiry block 180f. If the expiry window has not passed, the processor 160f returns to the query block 178f, while if the expiry window has passed, the processor 160f proceeds to flash the red warning LED 32f and extinguish the yellow LED 30f as indicated on block 182f.

An inquiry is then made as to whether the post expiry window has passed, as indicated in an inquiry block 181f. If the post expiry window has not passed, a further inquiry is made as to whether the reset switch has been closed for the requisite duration, as indicated in an inquiry block 183f.

If the reset switch has not been held for the requisite duration, the program returns to the inquiry block 181f, while if the reset switch has been closed for the requisite duration, the program proceeds with a resetting sequence to be described hereinafter.

If the post expiry window has expired, as determined in the inquiry block 181f, the processor flashes the red LED at an increased rate, as indicated in a block 185f.

An inquiry is then made as to whether or not the audible alarm has been programmed, as indicated in an inquiry block 184f. If the audible alarm has been programmed, the processor actuates the audible alarm, as indicated in a block 186f and proceeds to the next inquiry, which is whether or not the reset switch 42f has been pressed for the requisite duration, as indicated in an inquiry block 188f.

If the audible alarm was not programmed, the processor proceeds from inquiry block 184f directly to the inquiry block 188*f*. If the processor does not detect that the reset switch 42*f* has been pressed for the required duration in inquiry block 188*f*, the processor returns to the inquiry block 188*f*.

If the processor detects that the reset switch 42*f* has been pressed for the requisite duration, the processor proceeds with resetting the patient repositioning cycle, initiating the counter and disabling the LED's 30*f*, 32*f* as well as the audible alarm 84*f* as indicated in a block 190*f*. The processor additionally enters a low power standby mode as indicated in a block 192*a* and returns to the inquiry block 174*f*.

Figure 13:
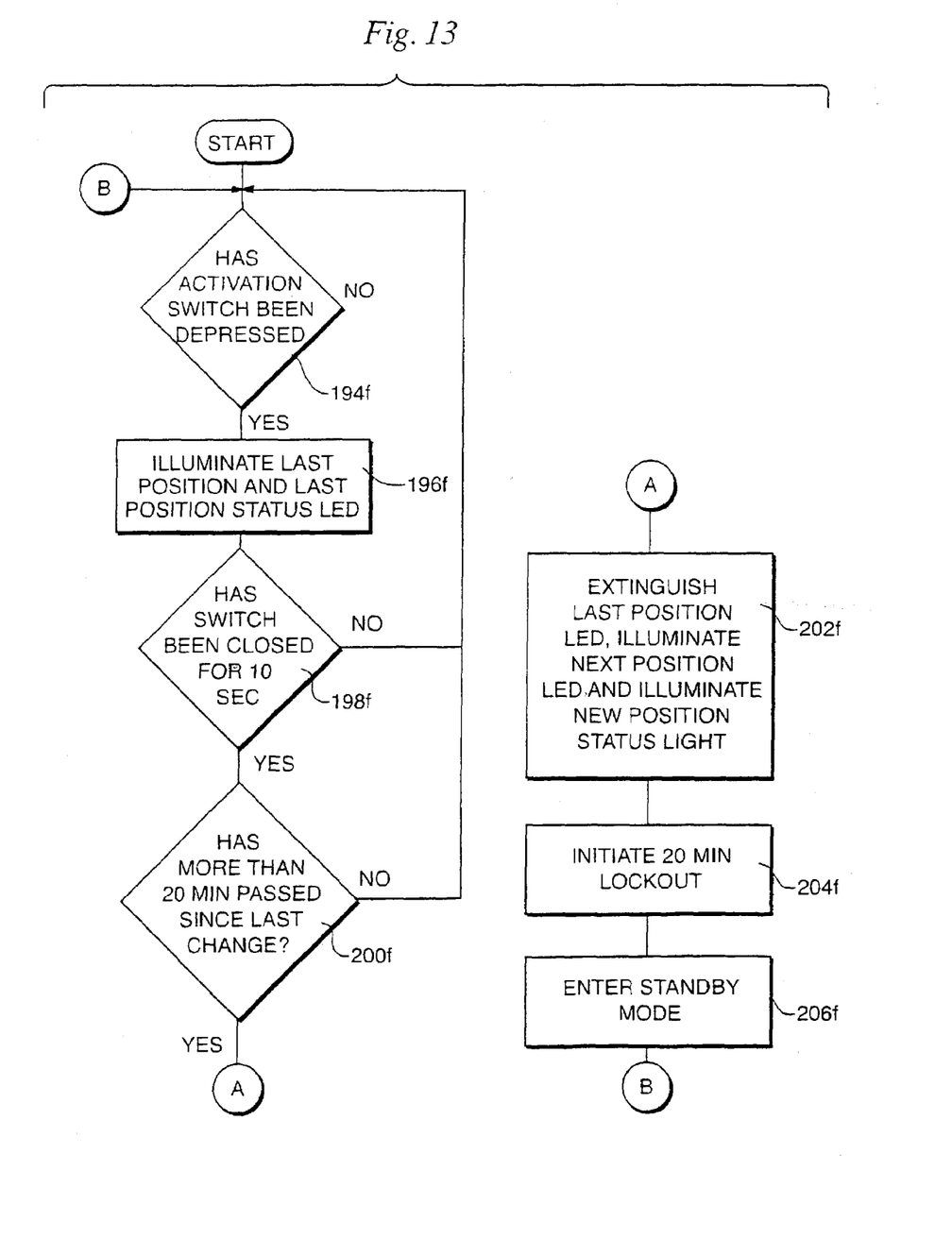
FIG. 13 is a schematized diagram of a typical routine for the processor implemented patient position sequence indicator.

Referring now to FIG. 13 which depicts a typical subroutine for the patient position indicator processor 170*f*, initially, an inquiry is made as to whether or not the actuation switch 76*f* has been depressed, as indicated in a block 194*f*. If the switch 76*f* has not been depressed, the processor returns to the inquiry block 194*f*. If, on the other hand, the actuation switch has been pressed, the processor proceeds to illuminate the last position indicator 66*a*, 68*a* or 70*a* and at the same time, the last position status light, as indicated in a block 196*f*.

The processor 170*f* thereafter proceeds to inquire if the switch 76*f* has been pressed for the requisite duration as indicated in a block 198*f*. The processor returns to the initial inquiry block 194*f* if the requisite duration has not passed.

If, on the other hand, the switch 76*f* has been held for the requisite duration, the processor proceeds to an inquiry block 200*f* to determine if more than 20 minutes has passed since the last patient position change. If less than 20 minutes has passed, the processor returns to the block 194*f*, while if more than 20 minutes has passed, the processor proceeds to extinguish the last position indicator light and status light and to illuminate the next sequential position indicator light and the new position status light, all as indicated in a block 202*f*.

The processor thereafter proceeds to initiate the 20 minute lock out, as indicated in a block 204*f* and enters a standby low power consumption mode as indicated in a block 206*f*. The processor 170*f* thereafter returns to the block 194*f*.

It should be appreciated that since both the annunciator and the patient position sequence indicator are stand alone, self-contained units, one may employ the processor implemented annunciator of the second embodiment with, for example, the patient position sequence indicator of the first embodiment.

A significant advantage of the annunciator and patient position sequence indicator is their low power consumption which results in eliminating the necessity of frequent battery changes which might necessitate interruption of the patient position turning regimen, removal of the equipment from the patient's room and/or the resetting of programmed patient position turning parameters.

Thus it will be seen that there is described a system for pressure ulcer prophylaxis and treatment which achieves the various aspects features and considerations of the present invention and which is well suited to meet the conditions of practical usage.

As various changes might be made in the illustrative embodiments herein disclosed without departing from the spirit of the invention, it is to be understood that all matter herein described or shown in the accompanying drawings is to be interpreted as illustrative and not in a limiting sense.

Having thus described the invention, there is claimed as new and desired to be secured by Letters Patent:

1. A system for pressure ulcer prophylaxis and treatment of a bedridden patient within a room, the system comprising an annunciator, the annunciator including a patient repositioning cycle timer, the cycle timer being resettable by a caregiver, the annunciator further including a caregiver attention directing device operatively coupled to the cycle timer, the caregiver attention directing device notifying the caregiver that the patient's position should be changed in response to a signal received from the cycle timer, the cycle timer generating the signal after a predetermined time interval relative to resetting the cycle timer, the annunciator being positioned externally of the room adjacent a doorway to the room, the system further including a patient position sequence indicator within the room and adjacent the patient, the patient position sequence indicator being preprogrammed with prescribed sequential patient turning positions, the patient position sequence indicator including a visual display of patient positions, the patient position sequence indicator being accessed by the caregiver to indicate the next sequential position to which the patient is to be placed by the caregiver after the caregiver receives notification from the attention directing device.

2. A system for pressure ulcer prophylaxis and treatment as constructed in accordance with claim 1 wherein the caregiver attention directing device comprises a visual indicator.

3. A system for pressure ulcer prophylaxis and treatment as constructed in accordance with claim 1 wherein the caregiver attention directing device comprises a sound generator.

4. A system for pressure ulcer prophylaxis and treatment as constructed in accordance with claim 1 wherein the cycle enters an expiry window after the predetermined time interval relative to resetting the cycle timer.

5. A system for pressure ulcer prophylaxis and treatment as constructed in accordance with claim 1 wherein the predetermined time interval relative to resetting the cycle timer comprises expiration of the cycle.

6. A system for pressure ulcer prophylaxis and treatment as constructed in accordance with claim 1 wherein a plurality of caregiver attention directing devices are provided and the cycle timer generates a plurality of signals at different predetermined time intervals relative to resetting the cycle timer, each attention directing device being operatively coupled to the cycle timer and being actuated responsive to a dedicated one of the plurality of signals.

7. A system for pressure ulcer prophylaxis and treatment as constructed in accordance with claim 1, the annunciator further including programming means for establishing the duration of a cycle, the programming means being operatively coupled to the cycle timer.

8. A system for pressure ulcer prophylaxis and treatment as constructed in accordance with claim 1 wherein the cycle timer comprises a pulse generator operatively coupled to a counter, the counter generating the signal received by the attention directing device.

9. A system for pressure ulcer prophylaxis and treatment as constructed in accordance with claim 1 wherein the cycle timer comprises a processor.

10. A system for pressure ulcer prophylaxis and treatment as constructed in accordance with claim 1 wherein the cycle timer is resettable by the caregiver only after the predetermined time interval has passed.

11. A system for pressure ulcer prophylaxis and treatment as constructed in accordance with claim 1 wherein the annunciator is self-contained within a single housing.

12. In a healthcare environment wherein a bedridden patient is situate in a room having a doorway, the improvement comprising an annunciator positioned exteriorly of the room adjacent or at the doorway in an area frequented by a patient caregiver, the annunciator being self-contained within a housing, the annunciator including a cycle timer, a caregiver actuated switch being operatively coupled to the cycle timer, the cycle timer being resettable by the caregiver actuated switch, the annunciator further including a caregiver attention directing device operatively coupled to the cycle timer, the cycle timer generating a signal after a predetermined time interval relative to resetting the cycle timer, the caregiver attention directing device receiving the cycle timer signal and in response thereto, generating an attention directing signal which notifies the caregiver to administer to the patient a prescribed treatment, the cycle timer being unresponsive to the caregiver actuated switch prior to completion of the predetermined time interval.

13. The improvement as constructed in accordance with claim 12 further including visual indicia within the room and adjacent the patient's bed, the visual indicia being representative of the treatment to be provided by the caregiver in response to the attention directing signal.

14. An annunciator as constructed in accordance with claim 12 wherein the cycle timer is unresponsive to the caregiver actuated switch unless the switch remains continuously actuated for a predetermined period.

15. An annunciator as constructed in accordance with claim 12 wherein the cycle tinier comprises a pulse generating circuit operatively connected to a counter circuit, the counter circuit generating the cycle timer signal.

16. In a healthcare environment wherein a bedridden patient is situate in a room having a doorway, the improvement comprising a system for pressure ulcer prophylaxis and treatment, the system including an annunciator positioned adjacent or at a doorway in an area frequented by a patient caregiver, the annunciator including a cycle timer, a caregiver actuated switch and a caregiver attention directing device, the caregiver actuated switch and the attention directing device being operatively coupled to the cycle timer, the system further including a patient position sequence indicator within the room and in proximity to the patient, the patient position sequence indicator including a visual display of sequential patient positions, the patient position sequence indicator being preprogrammed with an order of patient positions to be sequentially displayed, the patient position sequence indicator further including a caregiver actuated switch, the patient position sequence indicator sequentially advancing the visual display of patient positions to the next preprogrammed patient position in response to the actuation of the caregiver actuated switch.

17. The system for pressure ulcer prophylaxis and treatment as constructed in accordance with claim 16 wherein the patient position sequence indicator advances the display of patient positions only when the caregiver actuated switch remains continuously actuated for a predetermined period.

18. The system for pressure ulcer prophylaxis and treatment as constructed in accordance with claim 17 wherein the patient position sequence indicator displays the current patient position in response to the actuation of the caregiver actuated switch for a duration less than the predetermined period.

19. The system for pressure ulcer prophylaxis and treatment as constructed in accordance with claim 16 wherein the patient position sequence indicator advances the display of patient positions in response to actuation of the caregiver actuated switch only after a predetermined time interval relative to the preceding advancement of the displayed patient position.

* * * * *